United States Patent
Chen et al.

(10) Patent No.: US 10,233,144 B2
(45) Date of Patent: Mar. 19, 2019

(54) CRYSTALLINE FORM OF AHU377, PREPARATION METHOD AND USE THEREOF

(71) Applicant: CRYSTAL PHARMATECH CO., LTD., Suzhou, Jiangsu (CN)

(72) Inventors: Minhua Chen, Jiangsu (CN); Yanfeng Zhang, Jiangsu (CN); Chaohui Yang, Jiangsu (CN); Shu Yu, Jiangsu (CN); Xiaoyu Zhang, Jiangsu (CN); Liang Zhang, Shanghai (CN)

(73) Assignee: Crystal Pharmatech Co., Ltd., Suzhou (CN)

( * ) Notice: Subject to any disclaimer, the term of this patent is extended or adjusted under 35 U.S.C. 154(b) by 0 days.

(21) Appl. No.: 15/559,824

(22) PCT Filed: Mar. 18, 2016

(86) PCT No.: PCT/CN2016/076660
§ 371 (c)(1),
(2) Date: Sep. 19, 2017

(87) PCT Pub. No.: WO2016/150337
PCT Pub. Date: Sep. 29, 2016

(65) Prior Publication Data
US 2018/0086695 A1 Mar. 29, 2018

(30) Foreign Application Priority Data
Mar. 20, 2015 (CN) .......................... 2015 1 0124555

(51) Int. Cl.
| | | |
|---|---|---|
| A61K 31/41 | (2006.01) | |
| A61K 47/54 | (2017.01) | |
| A61K 47/55 | (2017.01) | |
| A61K 31/216 | (2006.01) | |
| C07C 231/24 | (2006.01) | |
| C07C 233/47 | (2006.01) | |
| C07C 235/74 | (2006.01) | |
| C07D 257/04 | (2006.01) | |

(52) U.S. Cl.
CPC .......... *C07C 235/74* (2013.01); *A61K 31/216* (2013.01); *A61K 31/41* (2013.01); *A61K 47/542* (2017.08); *A61K 47/545* (2017.08); *A61K 47/55* (2017.08); *C07C 231/24* (2013.01); *C07C 233/47* (2013.01); *C07D 257/04* (2013.01); *C07B 2200/13* (2013.01)

(58) Field of Classification Search
CPC ... C07C 233/47; C07C 235/74; C07C 231/24; C07B 2200/13; C07D 257/04
See application file for complete search history.

(56) References Cited

U.S. PATENT DOCUMENTS

| | | | | |
|---|---|---|---|---|
| 5,217,996 A | * | 6/1993 | Ksander ................ | C07C 233/47 514/533 |
| 2009/0156585 A1 | * | 6/2009 | Feng .................... | A61K 31/216 514/223.5 |

FOREIGN PATENT DOCUMENTS

| | | |
|---|---|---|
| CN | 101098689 A | 1/2008 |
| CN | 104230865 A | 12/2014 |
| CN | 104557600 A | 4/2015 |
| JP | 2008542447 A | 11/2008 |

OTHER PUBLICATIONS

International Search Report and Written Opinion of PCT Application No. PCT/CN2016/076660 dated Jun. 23, 2016.
Noriaki Hirayama, Organic Compound Crystal Production Manual: Principle and Know-How, Maruzen Co., Ltd., Japan, Jul. 25, 2008, p. 17-23, 37-40, 45-51, 57-65.
Teruzo Asahara, Solvent Handbook, 6th ed., Kodansha Scientific Ltd., Japan, 1985, p. 47-51.

* cited by examiner

*Primary Examiner* — Pancham Bakshi
*Assistant Examiner* — Mark R Luderer
(74) *Attorney, Agent, or Firm* — VLP Law Group LLP; Kent H. Cheng

(57) ABSTRACT

The present disclosure relates to a novel crystalline form of a compound of formula (I), preparation method and use thereof. The novel crystalline form in the present disclosure has good stability, low hygroscopicity, and remarkable purification effect in process. The novel crystalline form of the compound of formula (I) provided by the present disclosure can be used for the preparation of the drug for treating heart failure.

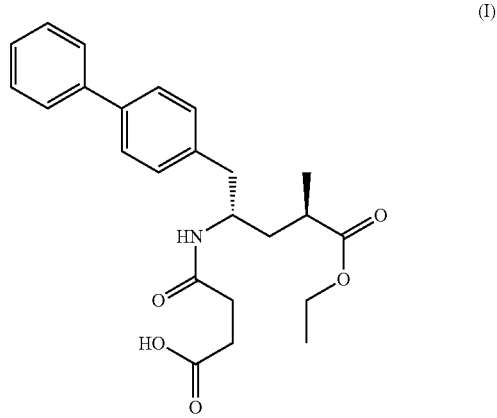

(I)

15 Claims, 3 Drawing Sheets

CRYSTALLINE FORM OF AHU377, PREPARATION METHOD AND USE THEREOF

TECHNICAL FIELD

The present disclosure relates to the field of pharmaceutical chemistry, particularly relates to crystalline form of AHU377, preparation method and use thereof.

BACKGROUND

The chemical name of AHU377 is (2R,4S)-5-(Biphenyl-4-yl)-4-[(3-carboxypropionyl)amino]-2-methylpentanoic acid ethyl ester, and the structure is shown as Formula (I):

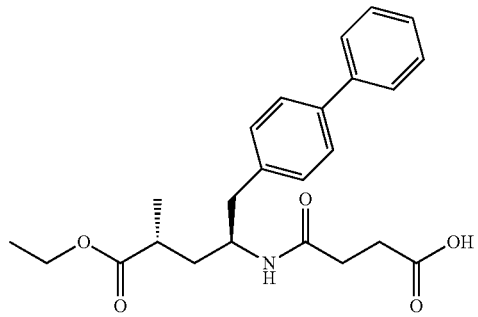

(I)

U.S. Pat. No. 5,354,892A firstly discloses the structure of AHU377, its sodium and the preparation method thereof, but the patent does not disclose crystalline forms of AHU377.

CN102702119A discloses a dual-acting compound LZ696, the structure is shown as Formula (II). The compound takes AHU377 and Valsartan as active ingredients, and the two active ingredients are connected through hydrogen bonds. The patent also discloses a method for preparing LCZ696 by using AHU377 or its salts. LCZ696 is clinically proven to be used for treating various cardiovascular and/or kidney diseases, and LCZ696 was approved in United States in 2015 as trade name "ENTRESTO".

The inventor summarized the prior art, and discovered that AHU377 was in the form of sticky oil at room temperature. Using AHU377 sticky oil as the starting material is hard to transfer and precisely quantify in the industrial production of LCZ696. According to the prior art, in order to overcome the problem of transfer and precise quantification, AHU377 has to be prepared into a solid salt, but the salt still needs to be broken into AHU377 free acid in the preparation of LCZ696 afterwards. The existing process is not only cumbersome, but also introduces a large number of impurity ions, which are bad for quality control in process.

Based on the problems of prior art, it is of great importance to find a solid form of AHU377, which is suitable for transferring, quantifying and avoiding introducing impurity ions and simplifying the process in the industrial production of LCZ696.

SUMMARY

The technical problem to be solved in the present disclosure is to provide a solid form of AHU377.

In order to solve the above-mentioned technical problems, the present disclosure uses the following technical solution:

A compound of formula (I),

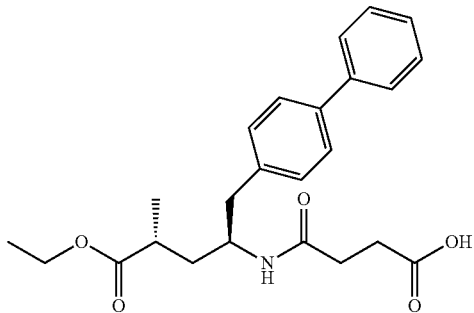

(I)

The compound of Formula (I) is in a solid form.
In particular, the compound of Formula (I) is in a crystalline form.

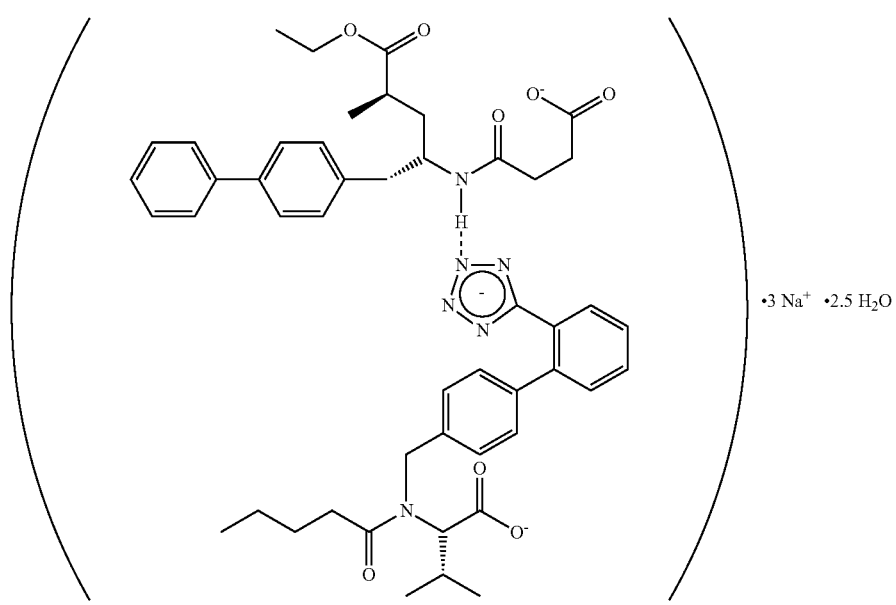

(II)

•3 Na$^+$ •2.5 H$_2$O

In particular, the compound of Formula (I) is an anhydrate, a hydrate or a solvate.

The solid form in the present disclosure is an anhydrate, designated as crystalline Form I. The crystalline form in the present disclosure has good stability and low hygroscopicity and is suitable for industrial production.

In particular, said solid form is crystalline Form I, and the X-ray powder diffraction pattern of Form I shows characteristic peaks at 2theta values of 17.2±0.2°, 16.4±0.2° and 9.8±0.2°.

Preferably, the X-ray powder diffraction pattern of crystalline Form I shows characteristic peaks at 2theta values of 12.3°±0.2°, 8.2°±0.2° and 4.1°±0.2°.

More preferably, the X-ray powder diffraction pattern of crystalline Form I shows characteristic peaks at 2theta values of 13.0°±0.2°, 18.4°±0.2°, 13.8°±0.2° and 6.1±0.2°.

In particular, the X-ray powder diffraction pattern of crystalline Form I shows characteristic peaks at 2theta values of 17.2±0.2°, 16.4±0.2°, 9.8±0.2°, 12.3°±0.2°, 8.2°±0.2°, 4.1°±0.2°, 13.0°±0.2°, 18.4°±0.2°, 13.8°±0.2° and 6.1±0.2°.

The X-ray powder diffraction pattern of the crystalline Form I of the present disclosure is substantially as depicted in FIG. 1.

The differential scanning calorimetry (DSC) thermogram of crystalline Form I shows an endothermic peak when heated to around 72° C. (onset temperature), which is substantially as depicted in FIG. 2.

The thermal gravimetric analysis (TGA) thermogram of crystalline Form I of the present disclosure shows about 0.9% weight loss when heated to 140° C., which is substantially as depicted in FIG. 3.

The present disclosure further provides a process for preparing solid form of Formula (I), the solid form of Formula (I) is precipitated by crystallization of the sticky oil of Formula (I) in a mixture of one or more organic solvents of alcohols, ethers, ketones, aromatic hydrocarbons, with one or two solvents of alkanes, water.

Preferably, said mixture is a mixture of toluene and n-heptane.

More preferably, the sticky oil of Formula (I) is firstly dissolved in toluene, then n-heptane is added, and solid form of Formula (I) is precipitated by crystallization.

More preferably, the content of sticky oil in toluene is 0.1 to 0.2 g/mL.

Preferably, the crystallization methods comprise the steps of anti-solvent addition, evaporation, stirring or cooling.

The present disclosure further provides use of the solid form of Formula (I) for preparing a drug for treating heart failure.

The disclosure further provides a drug for treating heart failure, wherein active ingredient of the drug is a complex which comprising valsartan and the solid form of Formula (I).

The present disclosure also provides a process for preparing a drug for treating heart failure, comprising reacting the solid form of Formula I, Valsartan and the alkaline containing sodium ions in ketone solvents or a mixture of ketone solvents and water to obtain the drug for treating heart failure.

Preferably, the mass ratio of the solid form of Formula (I) and Valsartan is from 1.1:1 to 1:1.1.

Preferably, said alkaline containing sodium ion comprises sodium hydroxide.

Preferably, said ketone solvent comprises acetone.

Furthermore, the water content of the reaction system is no more than 6%.

The present disclosure has the following advantages:

AHU377 prepared according to the prior art is sticky oil and no crystalline form of AHU377 is seen in patent or literature. The inventors studied and discovered a crystalline form suitable for development. The AHU377 crystalline form prepared in the present disclosure has good stability, low hygroscopicity, strong impurity removing capacity, remarkable effect of purification, and strong economic value.

The AHU377 crystalline form prepared by the present disclosure can be used for the preparation of LCZ696, a drug for treating heart failure. It overcomes the difficulties that using AHU377 sticky oil as the starting material in the prior art is hard to transfer and precisely quantify. It also simplifies the preparation method, and avoids introducing impurity ions, which is of great significance to the industrial production and quality control of LCZ696.

DETAILED DESCRIPTION

The present disclosure will be further explained by the specific embodiments, but are not intended to limit the scope of the present disclosure. The skilled in the art can make improvements to the process of preparation and the used instruments within the scope of the claims, and those improvements should be considered as falling into the scope of the present disclosure. Therefore, the protective scope of the present disclosure patent should be defined by the claims.

In the following examples, the test methods are generally carried out in accordance with conventional conditions or conditions recommended by the manufacturer. The starting material of AHU377 is a sticky oil prepared according to the prior art, for example U.S. Pat. No. 5,354,892A, and the remaining raw materials are commercially available.

The abbreviations used in the disclosure are explained as follows:

XRPD: X-ray Powder Diffraction
DSC: Differential Scanning calorimetry
TGA: Thermal Gravimetric Analysis
DVS: Dynamic Vapor Sorption
PLM: Polarized Light Microscope X-ray powder diffraction pattern in the present disclosure was acquired by Panalytical Empyrean X-ray powder diffraction, and the detection temperature was room temperature (about 25° C.). The parameters of the X-ray powder diffraction method of the present disclosure were as follows:

X-ray reflection parameters: CuKa
Kα1 (Å): 1.540598; Kα2 (Å): 1.544426
Kα2/Kα1 intensity ratio: 0.50
Voltage: 45 (kV)
Current: 40 (mA)
Divergence slit: automatic Scan mode: Continuous
Scan range: from 3.0° to 40.0°

Differential scanning calorimetry (DSC) thermogram in the present disclosure was acquired by a TAQ2000. The parameters of the differential scanning calorimetry method of the present disclosure were as follow:

The scan rate: 10° C./min
Purge gas: nitrogen

Thermal gravimetric analysis (TGA) thermogram in the present disclosure was acquired by a TAQ5000. The parameters of the thermal gravimetric analysis (TGA) method of the present disclosure were as follow:

The scan rate: 10° C./min
Purge gas: nitrogen

Dynamic Vapor Sorption (DVS) was measured via a SMS (Surface Measurement Systems) DVS Intrinsic. Typical Parameters for DVS test are listed below.

Temperature: 25° C.
Gas and flow rate: N$_2$, 200 mL/min
dm/dt: 0.002%/min
RH range: 0% RH to 95% RH Example 1

Process for Preparing Crystalline Form I of AHU377:

801.8 mg of AHU377 was dissolved into 5 mL of toluene, then 5 mL of n-heptane was added. After stirring overnight under 4° C., Form I was obtained.

Figure 1:
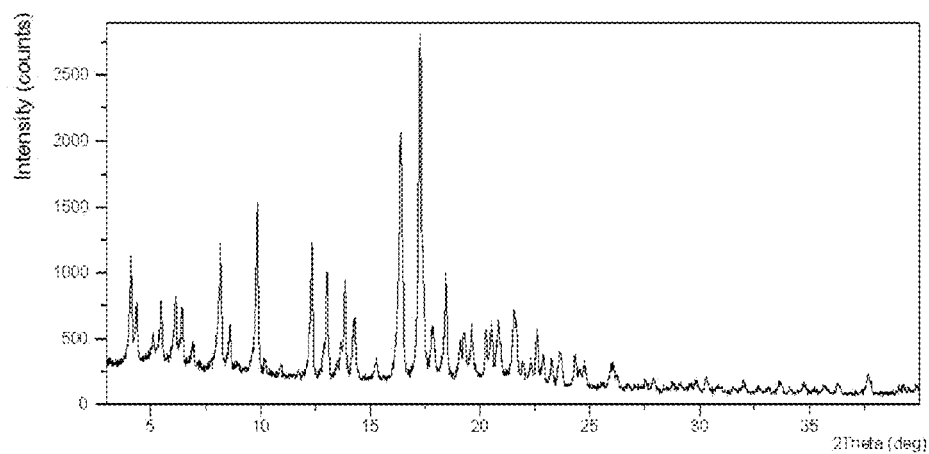
FIG. 1 shows the XRPD pattern of AHU377 crystalline Form I prepared in Example 1.
Figure 2:
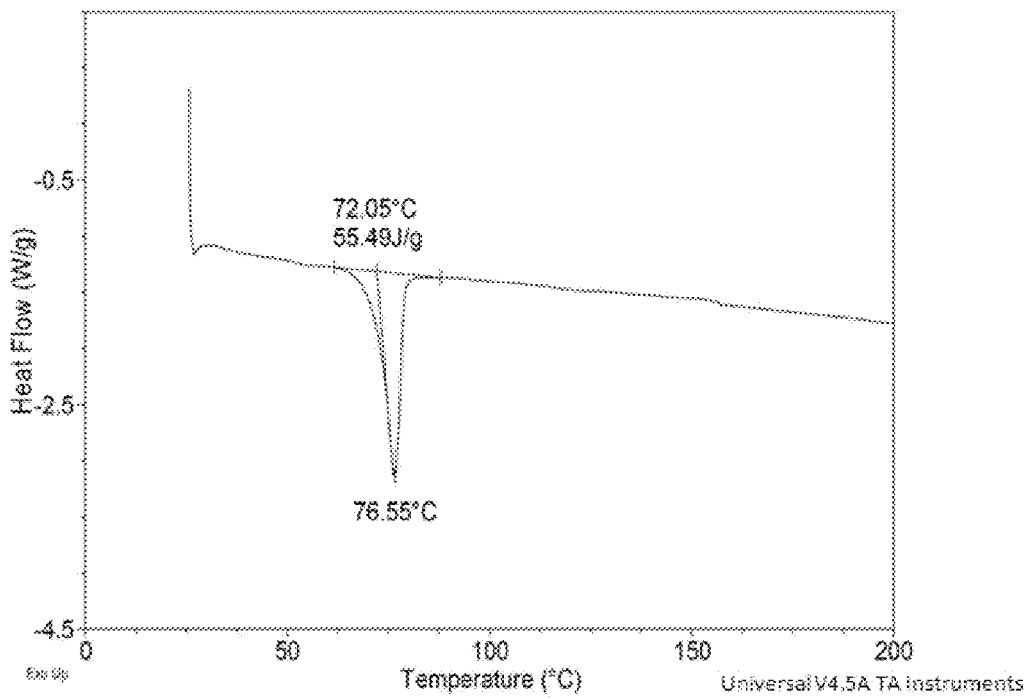
FIG. 2 shows the DSC thermogram of AHU377 crystalline Form I prepared in Example 1.
Figure 3:
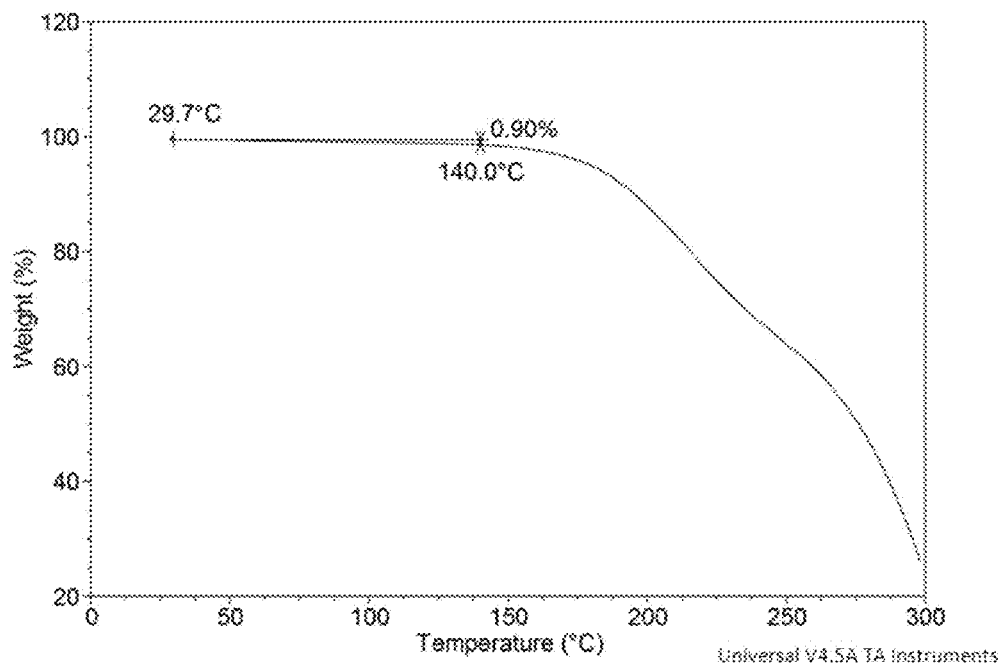
FIG. 3 shows the TGA thermogram of AHU377 crystalline Form I prepared in Example 1.

The X-ray powder diffraction (XRPD) data is displayed in Table 1. The X-ray powder diffraction (XRPD) pattern is displayed in FIG. 1, DSC thermogram is displayed in FIG. 2, and TGA thermogram is displayed in FIG. 3.

TABLE 1

| 2theta | d spacing | intensity % |
|---|---|---|
| 4.09 | 21.63 | 37.77 |
| 4.34 | 20.38 | 25.44 |
| 5.07 | 17.44 | 16.66 |
| 5.44 | 16.26 | 25.99 |
| 6.11 | 14.46 | 26.56 |
| 6.39 | 13.82 | 23.70 |
| 6.89 | 12.83 | 13.96 |
| 8.15 | 10.84 | 40.06 |
| 8.58 | 10.30 | 18.80 |
| 9.83 | 9.00 | 52.19 |
| 10.17 | 8.70 | 9.34 |
| 10.89 | 8.12 | 7.89 |
| 12.31 | 7.19 | 41.81 |
| 13.00 | 6.81 | 33.85 |
| 13.82 | 6.41 | 30.86 |
| 14.27 | 6.21 | 20.37 |
| 15.25 | 5.81 | 9.01 |
| 16.36 | 5.42 | 71.29 |
| 17.24 | 5.14 | 100.00 |
| 17.82 | 4.98 | 18.96 |
| 18.42 | 4.82 | 33.68 |
| 19.05 | 4.66 | 14.82 |
| 19.25 | 4.61 | 16.49 |
| 19.60 | 4.53 | 19.15 |
| 20.24 | 4.39 | 17.56 |
| 20.47 | 4.34 | 19.84 |
| 20.82 | 4.27 | 18.95 |
| 21.52 | 4.13 | 23.00 |

TABLE 1-continued

| 2theta | d spacing | intensity % |
|---|---|---|
| 21.93 | 4.05 | 8.30 |
| 22.28 | 3.99 | 9.61 |
| 22.55 | 3.94 | 18.26 |
| 22.84 | 3.89 | 10.60 |
| 23.25 | 3.83 | 8.86 |
| 23.60 | 3.77 | 11.13 |
| 24.31 | 3.66 | 10.10 |
| 24.73 | 3.60 | 7.97 |
| 26.03 | 3.42 | 7.84 |
| 27.49 | 3.24 | 4.04 |
| 27.86 | 3.20 | 4.20 |
| 28.78 | 3.10 | 2.65 |
| 29.81 | 3.00 | 3.44 |
| 30.27 | 2.95 | 4.40 |
| 30.84 | 2.90 | 1.85 |
| 31.99 | 2.80 | 3.81 |
| 32.67 | 2.74 | 1.72 |
| 33.10 | 2.71 | 1.36 |
| 33.65 | 2.66 | 2.95 |
| 34.10 | 2.63 | 1.06 |
| 34.72 | 2.58 | 3.24 |
| 35.66 | 2.52 | 1.87 |

Example 2

Process for Preparing Crystalline Form I of AHU377:

510 mg of AHU377 (the initial purity was 98.74%) was dissolved into 3 mL of toluene to get a clear solution, then 3 mL of n-heptane was gradually added, and the seed of crystalline form I of AHU377 was added during the procedure. Form I was obtained by stirring at room temperature (25° C.). The purity of AHU377 crystalline form I final product was 99.64%.

Process for preparing crystalline Form I can play an important role in the purification of API. It was found that the purity was improved from 98.74% to 99.64% through HPLC purity test, and the purification effect was remarkable.

The X-ray powder diffraction (XRPD) data in this example is displayed in Table 2.

TABLE 2

| 2theta | d spacing | intensity % |
|---|---|---|
| 4.09 | 21.62 | 32.91 |
| 4.33 | 20.41 | 29.77 |
| 5.43 | 16.28 | 29.01 |
| 6.11 | 14.46 | 19.82 |
| 6.39 | 13.83 | 28.42 |
| 6.87 | 12.87 | 10.47 |
| 8.18 | 10.81 | 26.73 |
| 8.58 | 10.30 | 14.88 |
| 9.87 | 8.97 | 40.46 |
| 12.32 | 7.18 | 37.11 |
| 13.01 | 6.80 | 44.62 |
| 13.85 | 6.40 | 31.80 |
| 14.21 | 6.23 | 20.05 |
| 15.22 | 5.82 | 9.19 |
| 16.40 | 5.40 | 62.77 |
| 17.27 | 5.14 | 100.00 |
| 17.83 | 4.98 | 20.31 |
| 18.45 | 4.81 | 19.96 |
| 19.24 | 4.61 | 17.64 |
| 19.63 | 4.52 | 12.80 |
| 20.26 | 4.38 | 10.28 |
| 20.81 | 4.27 | 19.68 |
| 21.48 | 4.14 | 23.13 |
| 22.58 | 3.94 | 12.92 |
| 22.85 | 3.89 | 8.70 |
| 23.23 | 3.83 | 9.03 |
| 23.63 | 3.77 | 8.94 |

TABLE 2-continued

| 2theta | d spacing | intensity % |
|---|---|---|
| 24.36 | 3.65 | 7.34 |
| 24.76 | 3.60 | 7.34 |
| 25.92 | 3.44 | 5.87 |
| 27.88 | 3.20 | 3.90 |
| 29.12 | 3.07 | 3.04 |
| 30.28 | 2.95 | 5.03 |
| 36.32 | 2.47 | 2.19 |
| 37.71 | 2.39 | 3.21 |

Example 3

Process for Preparing Crystalline Form I of AHU377:

2.02 g of AHU377 (the initial purity was 98.74%) was dissolved into 20 mL of toluene to get a clear solution, then 10 mL of n-heptane was gradually added, and the seed of crystalline form I of AHU377 was added during the procedure. Form I was obtained by stirring at room temperature (25° C.). The purity of crystalline form I final product was 99.69%.

The X-ray powder diffraction (XRPD) data in this example is displayed in Table 3.

TABLE 3

| 2theta | d spacing | intensity % |
|---|---|---|
| 4.09 | 21.61 | 43.10 |
| 4.33 | 20.43 | 27.42 |
| 5.05 | 17.52 | 14.43 |
| 5.42 | 16.29 | 23.58 |
| 6.10 | 14.49 | 18.20 |
| 6.42 | 13.77 | 18.18 |
| 6.90 | 12.81 | 8.81 |
| 8.13 | 10.88 | 25.69 |
| 8.58 | 10.31 | 13.18 |
| 9.90 | 8.94 | 30.22 |
| 10.89 | 8.12 | 4.92 |
| 12.31 | 7.19 | 29.62 |
| 13.02 | 6.80 | 28.37 |
| 13.86 | 6.39 | 26.57 |
| 14.22 | 6.23 | 18.20 |
| 15.25 | 5.81 | 8.51 |
| 16.40 | 5.41 | 62.51 |
| 17.30 | 5.13 | 100.00 |
| 17.84 | 4.97 | 22.96 |
| 18.45 | 4.81 | 24.70 |
| 19.28 | 4.60 | 23.11 |
| 19.64 | 4.52 | 16.76 |
| 20.31 | 4.37 | 16.22 |
| 20.54 | 4.32 | 18.27 |
| 20.85 | 4.26 | 24.69 |
| 21.59 | 4.12 | 28.98 |
| 22.60 | 3.93 | 17.07 |
| 23.67 | 3.76 | 12.55 |
| 24.36 | 3.65 | 11.74 |
| 24.78 | 3.59 | 10.78 |
| 26.02 | 3.42 | 11.14 |
| 27.93 | 3.19 | 5.64 |
| 29.16 | 3.06 | 4.64 |
| 30.34 | 2.95 | 5.14 |
| 32.10 | 2.79 | 2.71 |
| 33.74 | 2.66 | 3.66 |
| 34.77 | 2.58 | 2.64 |
| 35.76 | 2.51 | 2.66 |
| 36.36 | 2.47 | 5.06 |
| 37.75 | 2.38 | 6.14 |

Example 4

Process for Preparing LCZ696 Using Crystalline Form I of AHU377:

10.1 mg of AHU377 crystalline Form I and 10.2 mg of Valsartan were added to a glass vial, then 3.1 mg of NaOH was added, then 1.0 mL of acetone was added. Isolate the solids after stirring at room temperature (25° C.) overnight and LCZ696 was obtained.

Example 5

Process for Preparing LCZ696 Using Crystalline Form I of AHU377:

201.0 mg of AHU377 crystalline Form I and 213.4 mg of Valsartan were dissolved in 4 mL of acetone to get a clear solution, and 135 μL of sodium hydroxide aqueous solution (the mass ratio of sodium hydroxide and water is 1:2) was added, then it was stirred at 40° C. and the seed of LCZ696 was added during the procedure, LCZ696 was obtained after stirring for 3 hours.

Example 6

Process for Preparing LCZ696 Using Crystalline Form I of AHU377:

202.2 mg of AHU377 crystalline Form I and 222.1 mg of Valsartan were dissolved in 4 mL of acetone at room temperature (25° C.) to get a clear solution, and 135 μL of sodium hydroxide aqueous solution (the mass ratio of sodium hydroxide and water is 1:2) was gradually added, and the seed of LCZ696 was added during the procedure. Finally 4 mL of acetone was added, LCZ696 was obtained by stirring at room temperature (25° C.) for 2.5 hours. Impurity content of the final product was only 0.14%.

Figure 7:
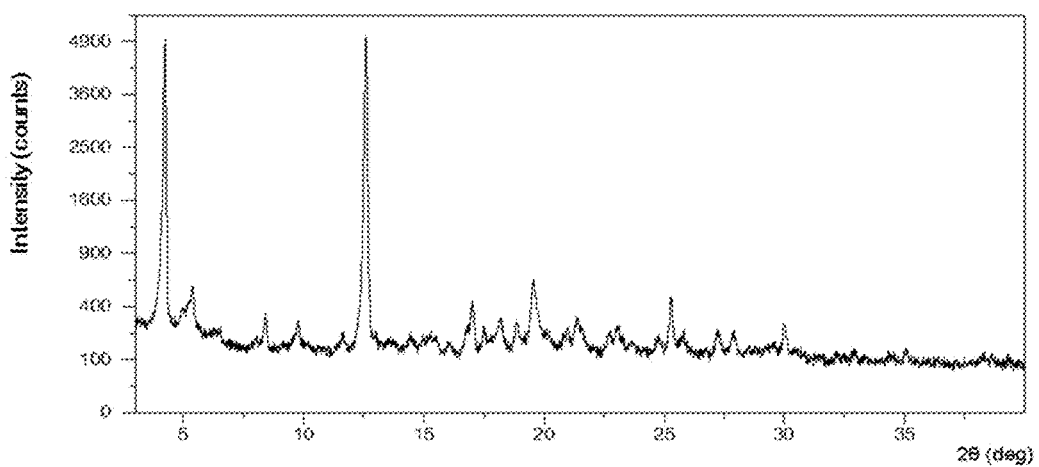
FIG. 7 shows an XRPD pattern of LCZ696 prepared in Example 6.

The X-ray powder diffraction (XRPD) pattern of LCZ696 in this example is displayed in FIG. 7.

Example 7

Figure 4:
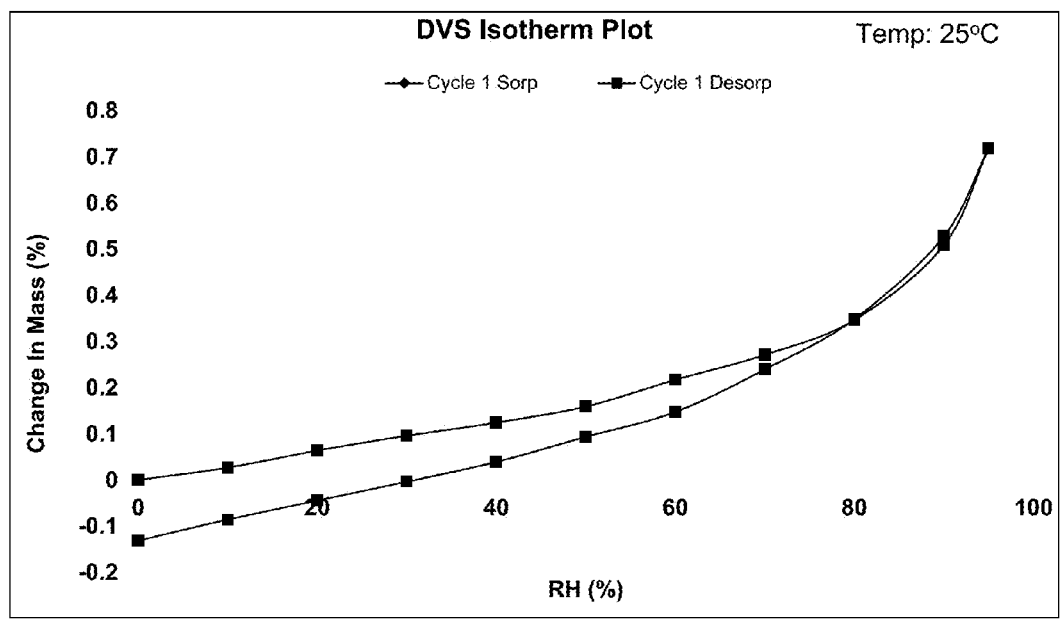
FIG. 4 shows the DVS plot of AHU377 crystalline Form I prepared in Example 1.

Hygroscopicity Assessment of AHU377 Crystalline Form I:

10 mg of crystalline Form I of the present disclosure was tested using dynamic vapor sorption (DVS). The result is listed in Table. 4. The DVS isotherm plot of crystalline Form I is depicted in FIG. 4.

TABLE 4

| Solid Form | weight gain under 80% RH |
|---|---|
| Crystalline Form I of AHU377 | 0.35% |

About hygroscopicity characterization description and definition of hygroscopicity (Chinese Pharmacopoeia 2010 edition appendix XIX J Drug hygroscopic test guidelines, test at 25° C.±1° C., 80% Relative Humidity)
  deliquescent: sufficient water is absorbed to form a liquid;
  very hygroscopic: increase in mass is equal to or greater than 15 percent;
  hygroscopic: increase in mass is less than 15 percent and equal to or greater than 2 percent;
  slightly hygroscopic: increase in mass is less than 2 percent and equal to or greater than 0.2 percent.
  no or almost no hygroscopic: increase in mass is less than 0.2 percent The result indicates that crystalline Form I of the present disclosure has a 0.35% weight gain at 80% RH. The hygroscopicity of crystalline Form I of AHU377 is slightly hygroscopic according to hygroscopic test guidelines.

Example 8

Figure 5:
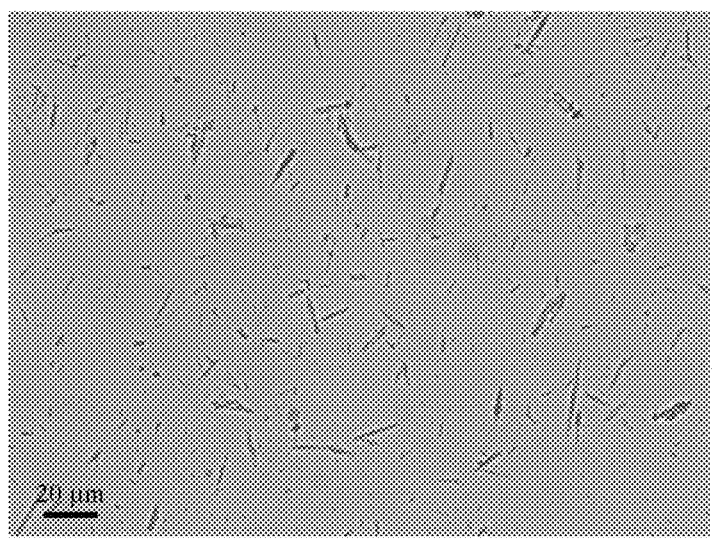
FIG. 5 shows the PLM image of AHU377 crystalline Form I prepared in Example 1.

Contrast of the Morphology of Crystalline Form I and Sticky Oil of AHU377:

The crystalline Form I of AHU377 obtained in example 1 in the present disclosure was photographed with PLM, and the figure shown in FIG. 5 indicates the crystalline Form I of AHU377 in the present disclosure has a needle-like shape and has good dispersibility.

Figure 6:
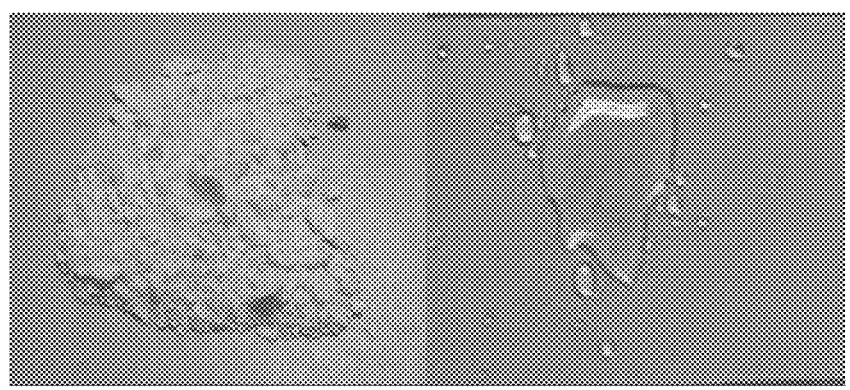
FIG. 6 shows contrast figure of the morphology of crystalline Form I and the sticky oil of AHU377, the left side of the picture shows crystalline Form I of AHU377 as a white powder, the right side of the picture shows sticky oil of AHU377, which is pale yellow and like sticky honey.

The contrast figure of the morphology of crystalline Form I and sticky oil of AHU377 was shown in FIG. 6, crystalline Form I of AHU377 was a white powder (the left side of FIG. 6), which was convenient to sample and quantify. While sticky oil of AHU377 was pale yellow and like sticky honey (the right side of FIG. 6), its surface is easy to harden at low temperature, thus it is difficult to sample and quantify.

What is claimed is:

1. The compound of Formula (I)

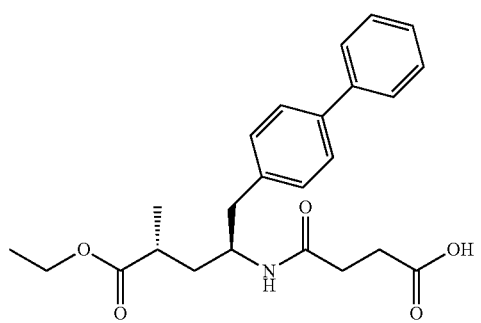

(I)

in the crystalline Form I, wherein the X-ray powder diffraction pattern of Form I shows characteristic peaks at 2theta values of 17.2±0.2°, 16.4±0.2° and 9.8±0.2°.

2. The compound of Formula (I) according to claim 1, wherein the X-ray powder diffraction pattern of Form I also shows characteristic peaks at 2theta values of 12.3°±0.2°, 8.2°±0.2° and 4.1°±0.2°.

3. The compound of Formula (I) according to claim 1, wherein the X-ray powder diffraction pattern of Form I also shows characteristic peaks at 2theta values of 13.0°±0.2°, 18.4°±0.2°, 13.8°±0.2° and 6.1±0.2°.

4. The compound of Formula (I) according to claim 1, wherein the X-ray powder diffraction pattern of Form I shows characteristic peaks at 2theta values of 17.2±0.2°, 16.4±0.2°, 9.8±0.2°, 12.3°±0.2°, 8.2°±0.2°, 4.1°±0.2°, 13.0°±0.2°, 18.4°±0.2°, 13.8°±0.2° and 6.1±0.2°.

5. A process for preparing solid form of the compound of Formula (I) according to claim 1, wherein the process comprises: the solid form of the compound of Formula (I) is precipitated by crystallization of an oil of Formula (I) in a mixture of one or more organic solvents of alcohols, ethers, ketones, aromatic hydrocarbons with one or two solvents of alkanes, water.

6. The process according to claim 5, wherein the mixture is a mixture of toluene and n-heptane.

7. The process according to claim 6, wherein the oil of the compound of Formula (I) is first dissolved in the toluene, then n-heptane is added, and solid form is precipitated by crystallization.

8. The process according to claim 7, wherein the content of oil in toluene is 0.1 to 0.2 g/mL.

9. The process according to claim 5, wherein the crystallization method comprises the steps of anti-solvent addition, evaporation, stirring or cooling.

10. A method of treating heart failure in a subject thereof, comprising administering the solid form of the compound of formula (I) according to claim 1 to the subject.

11. A drug for treating heart failure, wherein the active ingredient of the drug is a complex comprising valsartan and the solid form of the compound of formula (I) according claim 1.

12. A process for preparing the drug for treating heart failure according to claim 11, wherein the drug for treating heart failure is obtained by reacting the solid form of the compound of Formula (I), valsartan and alkaline containing sodium ion in ketone solvents or a mixture of ketone solvents and water.

13. The process for preparing the drug for treating heart failure according to claim 12, wherein the mass ratio of the compound of Formula (I) and valsartan is from 1.1:1 to 1:1.1.

14. The process for preparing the drug for treating heart failure according to claim 12, wherein said alkaline containing sodium ion comprises sodium hydroxide.

15. The process for preparing the drug for treating heart failure according to claim 12, wherein said ketone solvent comprises acetone.

* * * * *